United States Patent [19]

Quynn

[11] Patent Number: 5,254,406
[45] Date of Patent: Oct. 19, 1993

[54] FACEPAINT MATERIAL

[75] Inventor: Richard G. Quynn, Duxbury, Mass.

[73] Assignee: The United States of America as represented by the Secretary of the Army, Washington, D.C.

[21] Appl. No.: 962,765

[22] Filed: Oct. 19, 1992

[51] Int. Cl.$^5$ .................................................. B32B 9/00
[52] U.S. Cl. ...................................... 428/328; 428/323; 428/919; 106/14.33; 106/272; 106/403; 106/404; 106/499; 106/502; 106/504
[58] Field of Search ....................... 428/323, 328, 919; 106/14.33, 272, 403, 404, 499, 502, 504

[56] References Cited

U.S. PATENT DOCUMENTS

| 2,250,185 | 7/1941 | Mohler | 106/14 |
| 2,596,101 | 5/1952 | Pritzker | 106/24 |
| 4,289,677 | 9/1981 | Supcoe et al. | 260/33.6 SB |
| 4,495,239 | 1/1985 | Pusch et al. | 428/192 |
| 5,045,114 | 9/1991 | Bigalk et al. | 106/404 |

Primary Examiner—Patrick J. Ryan
Assistant Examiner—Marie R. Macholl
Attorney, Agent, or Firm—Richard J. Donahue

[57] ABSTRACT

A facepaint material for application to the skin of the human body to reduce the possibility of detection of the user by a thermal imaging device. The facepaint material comprises metallic particles embedded in a jelly-like vehicle having no strong radiation absorption bands in the 8–14 micrometer wavelength region.

8 Claims, No Drawings

FACEPAINT MATERIAL

The invention described herein may be manufactured, used and licensed by or for the Government for Governmental purposes without the payment to me of any royalty thereon.

BACKGROUND OF THE INVENTION

The present invention relates generally to skin covering material, referred to herein as facepaint material, and more particularly to a facepaint material especially formulated to prevent or substantially reduce the possibility of detection of the user thereof by thermal imaging devices.

While the present standard military camouflage facepaint provides protection against detection of soldiers by visible means and image intensifier-type night vision devices, there exists a need to eliminate or reduce the threat of detection of the soldier either during daylight or at night by thermal imaging devices.

Thermal imagery is a rapidly developing field of technology, and new applications for it are found almost every day. For background information on this subject, one of many texts of interest is entitled "Thermal Imaging Systems" by J. M. Lloyd, Plenum Press, New York and London, 1975. This text is incorporated herein by reference.

Thermal imagers pose a serious surveillance threat to any heat source. These devices depend for their operation on a temperature difference between the target, i.e. the heat source, and the ambient temperature. It is well-known in this art that the sensor of a thermal imager can detect any heat source whose temperature is different (usually greater) from its surroundings by about 2° F. (1.1° C.) or more. Thermal imagers thus "see" (produce an image of) smokestacks of fixed buildings, smokestacks of ships at sea, helicopters, airplanes landing at airports, buildings the infrared reflectivity of which may be different in different parts thereof (as illustrated in the Lloyd text referenced above), human faces, etc.

Thermal imagers are therefore a dangerous surveillance threat as modern tanks and airplanes are commonly equipped with them. One danger from the military viewpoint is that such imagers can easily detect a soldier's face or other exposed skin (at approx. 97° F.), his uniform, a heated tent, an armored vehicle not fully cooled down, airplane, etc. There is no contrast in thermal images of human faces to background only if the ambient temperature is coincidentally about 97° F. Their advantage over other devices is that since their operation depends on emitted, rather than reflected energy, they can "see" through obscurants, operate just as well during the day as at night, can detect a target completely hidden in a shadow, and can defeat ordinary (visible) camouflage. For the reasons advanced above, it becomes important to have a safe, inexpensive and effective means to minimize the possibility of detection of a soldier by detection of the high thermal contrast which often exists between his or her face and hands and the surrounding environment.

In order to avoid detection by a thermal imager device, it is necessary to reduce the difference in temperature ($\Delta T$) "seen" by the imager device. One practical way is to lower the emissivity of the target. Under these conditions the target appears "cooler" than is actually the case. Emissivity is an optical term referring to the efficiency of radiation. It has no units and can vary from 0 to 1.0. A hypothetical "black body" has an emissivity of 1.0, i.e., 100 percent.

SUMMARY OF THE INVENTION

The facepaint materials presently in use have an emissivity close to 1.0, that of the face alone. It has been found that by including metallic particles (which have an emissivity of about 0.1 or lower) in a facepaint material having specific absorption characteristics, an imager device can be "fooled" into indicating a temperature different from the actual face temperature.

It should be pointed out that ordinary metallic paint (that one might buy in a hardware store) has no effect on the thermal signature of the face. The reason is that when the paint dries, the metallic particles are coated with a thin film of the "vehicle", (the medium which carries or transports the metallic particle component of the present invention) the material of which absorbs infrared radiation of wavelength 8 to 14 micrometers, the detector range of the imager. The choice of "vehicle" is therefore critical and it must have no strong absorption bands in the 8-14 micrometer wavelength region. By "strong" absorption band is meant herein a percent of radiation absorption greater than five percent.

It is therefore the primary object of the present invention to provide a novel facepaint material that presents an effective deterrent to the detection of the user by thermal imager devices.

These and other objects are accomplished by providing a facepaint material comprised of a petroleum-based jelly-like vehicle having no strong absorption bands in the 8-14 micrometer region and having metallic particles contained therein.

DESCRIPTION OF THE DISCLOSED EMBODIMENTS

According to the present invention, a novel facepaint material is disclosed which the soldier applies to his or her face and (if no gloves are worn) hands, and which is formulated to substantially reduce their thermal normal emissivity of 0.97. The facepaint material comprises a jelly-like non-metallic carrier material, referred to herein as the "vehicle", having no strong absorption bands in the 8 to 14 micrometer wavelength region, and having metallic particles embedded therein. One such vehicle useful in the present invention is petrolatum, also known as petroleum jelly.

The precise percentages of the metal particles and petrolatum in a preferred embodiment of the invention is somewhat dependent upon the ambient temperature of the background that it is desired for the target to "match", i.e., show the same apparent temperature. For aluminum particles in petrolatum, about 35 percent by weight of aluminum powder in the facepaint material is optimal for a background temperature of 32° F. For a background temperature of 70° F., about 5 percent by weight of aluminum powder is optimum. Other metallic particles and other "vehicles" will provide different numbers.

Several facepaint formulations have been formulated using the following materials:

Aluminum Particles:
  ACS reagent Grade
  Alcan Division of Alcan Aluminum Corp, Grade MD 7100
Nickel Particles:
  Inco Specialty Powder Products, Saddle Brook, N.J.

Novamet Brown Nickel Pigment 87-008
Petrolatum:
 White Petrolatum USP Topical Lubricant
 E. Fougera and Co., Division of Byk-Golden Inc.
 Hicksville, N.Y. 11802
Ceresine Wax:
 Source unknown Petrolatum is described on page 1033 of the Merck Index 10th Edition, published by Merck and Co., 1983. Ceresine Wax is described in Military Specification MIL-P-2018G, dated Mar. 26, 1985. The aforementioned references are incorporated herein by reference.

These and other various formulations were applied to a stainless steel beaker maintained at body temperature (97° F.). Separate experiments indicated that the beaker surface reached this temperature. An Inframetrics Model 525 Thermal Imager was used to measure the emissivities. The experimental error was judged to be ±10%. Qualitative observations were made of formulations applied onto the skin. Quantitive measurements were made on formulations smeared onto the beaker. The results of the latter measurements are given in Table I, infra.

TABLE I

EMISSIVITY OF ALUMINUM/PETROLATUM FACEPAINT FORMULATIONS

| Wt. % of Aluminum Particles | Emissivity at 97° F. |
|---|---|
| 0.31% | 0.90 |
| 0.50 | 0.86 |
| 0.62 | 0.79 |
| 1.93 | 0.79 |
| 6.06 | 0.69 |
| 11.0 | 0.61 |
| 12.4 | 0.54 |
| 17.3 | 0.57 |
| 37.3 | 0.55 |
| 42.1 | 0.56 |
| 44.0 | 0.56, 0.65* |
| 48.0 | 0.48, 0.69* |

*At different thickness

Increasing the proportion of aluminum particles reduced somewhat the emissivity to about 0.5, but further reduction does not seem possible. A face emissivity of about 0.5 corresponded to an ambient temperature of 32° F. (freezing); that is, the imager device indicated an apparent target temperature of 32° F., rather than 97° F.

Measured emissivity values were affected somewhat by the roughness of the surface. It was found that the measured value depended on the thickness of the formulation, probably because of "radiation trapping", the thinnest application invariably causing the largest reduction. "Radiation trapping" refers to an optical effect which makes the target behave more like a black body (rase its emissivity).

It is presently believed that the choice of metallic particle is not critical. Aluminum is preferred because of its price, non-toxicity and easy availability. It is known, like other metals, to have a comparatively low emissivity at infrared wavelengths. Other finely divided metals might perform just as well. It was observed qualitatively that nickel particles (10.1% by wt. of total formulation) in petrolatum also lowered the face emissivity. The only limitation on the metal would appear to be the medical consequences of its getting into the bloodstream. Lead and mercury were avoided for this reason.

It is not believed that the particle size of the metal is critical. The nickel particles were about 94 micrometers in average diameter, as compared to about 10 micrometers for the aluminum particles, as measured by a scanning electron microscope. Both metals lowered the emissivity of the face.

A battery powered thermal imager (Inframetrics Model 525) was used to conduct some field measurements. However, precise quantitative field measurements could not be made, inasmuch as a portable standard "black body" radiator (known to have an emissivity of 1.0), capable or being set to any desired temperature, was not available. Therefore, qualitative, and not quantitative observations were made, observing the direction of the change, but not the precise amount.

Qualitatively, with about 15 and 100 feet between the person and the imager, a formulation of 40 percent aluminum and 60 percent petrolatum reduced the apparent temperature of the skin, at night, when the ambient temperature was about 66° F. A formulation of approximately 10 percent nickel particles and 90 percent petrolatum, likewise showed a reduction of the apparent temperature of the skin of the user. The observations were made during the day at a distance of 15 feet. The average diameter size of the nickel particles was 94 micrometers.

In one embodiment, a 4 percent by total weight quantity of aluminum particles was used together with ceresine wax. It likewise reduced the apparent temperature of the skin at a distance of 15 feet.

While preferred embodiments have been shown and described, various modifications and substitutions may be made thereto without departing from the spirit and scope of the invention. Accordingly, it is to be understood that the present invention has been described by way of illustration and not by way of limitation.

What is claimed is:

1. A facepaint material for application to the skin of the human body to reduce the possibility of detection of the user by a thermal imaging device, said facepaint material comprising a vehicle having a percentage radiation absorption of less than five percent in the 8 to 14 micrometer wavelength region and having nickel particles contained therein.

2. The facepaint material of claim 1 wherein said vehicle is ceresine wax.

3. The facepaint material of claim 1 wherein said vehicle is petrolatum.

4. A facepaint material for application to the skin of the human body to reduce the possibility of detection of the user by a thermal imaging device, said facepaint material comprising a ceresine wax vehicle having a percentage radiation absorption of less than five percent in the 8 to 14 micrometer wavelength region and having aluminum or nickel particles contained therein.

5. The facepaint material of claim 4 comprising particles of aluminum having a particle size of approximately ten micrometers in average diameter.

6. The facepaint material of claim 4 comprising particles of nickel having a particle size of approximately 94 micrometers in average diameter.

7. A facepaint material for application to the skin of the human body to reduce the possibility of detection of the user by a thermal imaging device, said facepaint material consisting essentially of aluminum particles suspended in petrolatum, said aluminum particles having a particle size of ten micrometers in average diameter and comprising in the aggregate about 35 percent of the total weight of said material, said petrolatum having a percentage radiation absorption of less than five percent in the 8-14 micrometer wavelength region.

8. A facepaint material for application to the skin of the human body to reduce the possibility of detection of the user by a thermal imaging device, said facepaint material consisting essentially of aluminum particles suspended in ceresine wax, said aluminum particles having a particle size of ten micrometers in average diameter and comprising in the aggregate about 4 percent of the total weight of said material, said ceresine wax having a percentage radiation absorption of less than five percent in the 8-14 micrometer wavelength region.

* * * * *